United States Patent
Chapelon et al.

(10) Patent No.: US 11,540,806 B2
(45) Date of Patent: Jan. 3, 2023

(54) DEVICE AND SYSTEM FOR GENERATING ULTRASONIC WAVES IN A TARGET REGION OF A SOFT SOLID AND METHOD FOR LOCALLY TREATING A TISSUE

(71) Applicants: INSTITUT NATIONAL DE LA SANTE ET DE LA RECHERCHE MEDICALE (INSERM), Paris (FR); UNIVERSITÉ CLAUDE BERNARD LYON 1, Villeurbanne (FR); CENTRE LÉON-BÉRARD, Lyons (FR)

(72) Inventors: Jean-Yves Chapelon, Lyons (FR); Jean-Louis Mestas, Lyons (FR); Cyril Lafon, Lyons (FR); Bernard Greillier, Lyons (FR); René Milleret, Pezenas (FR)

(73) Assignee: Centre Léon-Bérard, Lyons (FR)

( * ) Notice: Subject to any disclaimer, the term of this patent is extended or adjusted under 35 U.S.C. 154(b) by 189 days.

(21) Appl. No.: 15/763,717

(22) PCT Filed: Sep. 29, 2016

(86) PCT No.: PCT/EP2016/073191
§ 371 (c)(1),
(2) Date: Mar. 27, 2018

(87) PCT Pub. No.: WO2017/055403
PCT Pub. Date: Apr. 6, 2017

(65) Prior Publication Data
US 2018/0317884 A1    Nov. 8, 2018

(30) Foreign Application Priority Data
Sep. 29, 2015 (EP) .................................. 15306525

(51) Int. Cl.
  A61B 8/00      (2006.01)
  A61N 7/02      (2006.01)
  (Continued)

(52) U.S. Cl.
  CPC ............ *A61B 8/4483* (2013.01); *A61B 90/36* (2016.02); *A61B 90/37* (2016.02); *A61N 7/02* (2013.01);
  (Continued)

(58) Field of Classification Search
  CPC ....... A61B 8/4483; A61B 90/36; A61B 90/37; A61B 2090/378; A61B 2017/22008; A61N 7/02; A61N 2007/0078
  See application file for complete search history.

(56) References Cited

U.S. PATENT DOCUMENTS 5,146,923 A * 9/1992 Dhawan ................. A61B 5/444
                                                    600/476
5,879,314 A * 3/1999 Peterson ................ G10K 11/02
                                                    601/2
(Continued)

FOREIGN PATENT DOCUMENTS

EP    1795131 A1    6/2007
WO    2002/09813 A1    2/2002

OTHER PUBLICATIONS

Yang et al. "Analysis of dynamic high-frequency acoustic field control by metasurfaces lens", Nov. 22, 2019 (Year: 2019).*

*Primary Examiner* — Amanda Lauritzen Moher
*Assistant Examiner* — Brooke Lyn Klein
(74) *Attorney, Agent, or Firm* — WCF IP (57) ABSTRACT

This device (2) for generating ultrasonic waves in a target region of a soft solid, includes at least two ultrasound sources (32), light sources (40) distributed around a central axis (X2) of the device (2), for enlightening a zone of the
(Continued)

soft solid via subsurface scattering, and a video camera (50), for capturing images of the zone enlightened by the lighting means. The ultrasound source (32), the light sources (40) and the video camera (50) are mounted on a body of the device (20) and oriented toward a common target zone which includes a focal point of the ultrasound sources (32). A boresight of the video camera is aligned on the central axis (X2).

32 Claims, 6 Drawing Sheets

(51) Int. Cl.
  *A61B 90/00* (2016.01)
  *A61B 17/22* (2006.01)
  *A61N 7/00* (2006.01)
(52) U.S. Cl.
  CPC ............ *A61B 2017/22008* (2013.01); *A61B 2090/378* (2016.02); *A61N 2007/0078* (2013.01)

(56) References Cited

U.S. PATENT DOCUMENTS

| | | | |
|---|---|---|---|
| 9,436,993 B1* | 9/2016 | Stolka | A61B 5/742 |
| 2001/0031920 A1* | 10/2001 | Kaufman | G06T 19/00 600/431 |
| 2005/0154382 A1* | 7/2005 | Altshuler | A61B 90/36 606/9 |
| 2009/0306502 A1* | 12/2009 | Lacoste | A61B 8/4281 600/439 |
| 2010/0036292 A1* | 2/2010 | Darlington | A61N 7/00 601/2 |
| 2010/0094178 A1* | 4/2010 | Lacoste | A61B 5/4205 601/2 |
| 2010/0217161 A1* | 8/2010 | Shalgi | A61B 8/4245 601/2 |
| 2013/0131704 A1* | 5/2013 | Pechoux | A61N 7/02 606/169 |
| 2014/0213903 A1* | 7/2014 | Seo | A61B 34/32 600/439 |
| 2015/0065916 A1 | 3/2015 | Maguire et al. | |
| 2015/0173846 A1* | 6/2015 | Schneider | G02B 27/0101 600/424 |
| 2016/0287909 A1* | 10/2016 | Maxwell | A61B 8/0866 |

* cited by examiner

DEVICE AND SYSTEM FOR GENERATING ULTRASONIC WAVES IN A TARGET REGION OF A SOFT SOLID AND METHOD FOR LOCALLY TREATING A TISSUE

TECHNICAL FIELD OF THE INVENTION

This invention relates to a device for generating ultrasonic waves in a target region of a soft solid. The invention also relates to a system for generating ultrasonic waves, which includes such a device. Finally, this invention also relates to a method for locally treating a tissue of a subject with ultrasonic waves.

In the meaning of the present invention, a soft solid is an organic tissue which can have an animal or vegetal origin. For instance, such a soft solid can be an organ of a human body, of an animal body or of a vegetable.

BACKGROUND OF THE INVENTION

As mentioned in WO-A-2006/021651, ultrasounds can be used for the treatment of varicose veins. In such a case, a thermal effect of high-intensity ultrasound waves is used in order to shrink a vein wall.

A cavitation phenomenon can also be used. For instance, for the treatment of varicose veins, cavitation bubbles are created in order to generate local shock waves when they collapse. This allows destroying the endothelium of a given vein or vessel. In order to obtain a significant cavitation phenomenon, ultrasonic waves must be generated and focused at the right location. To this end, crossed ultrasonic beams can be used, as mentioned in EP-A-2 636 428.

Spider veins, that are close to the skin of a subject, are sometimes visible or partially visible. It is known to treat a vein at several points along its length in order to increase the efficiency of a treatment. However, when one places a treatment device on the skin of a subject or patient, this device hides the vein, so that the practitioner cannot accurately orientate and/or move the device in order to precisely focus ultrasonic waves on the venin, along its path.

As mentioned in WO-A-2014/160964, one can use an ultrasound imaging probe in order to detect a target within a soft body, this being based on an ultrasound technology. However, such an ultrasonic probe is expensive and hardly detects a vein with a small diameter, where blood flows with a low flow rate. Actually, a vein where blood has a low flow rate is difficult, and sometimes impossible, to detect via Doppler or B-mode ultrasound technology. Actually, the smaller a vein is and the lower the blood flow rate in a vein is, the more difficult and the more costly the detection is.

On the other hand, WO-A-2009/112969 and WO-A-2012/156863 rely on the application of high intensity focused ultrasound (HIFU) with different types of ultrasound sources. They do not allow precisely controlling where the ultrasonic waves are applied.

EP-A-1 795 131 discloses a HIFU system which includes a treatment head with a light source illuminating the skin of a patient. Such a construction does not allow obtaining a clear image of an object located below the skin, such as a vein. Moreover, a single ultrasound transducer is used, which implies that the cavitation zone obtained at its focal point might be unstable. In addition, as visible for instance on FIG. 3 of this document, the light source is radially offset from an imaging unit, which does not allow precise enlightening of an object to be viewed.

WO-A-02/09813 discloses a method and a device for epilation where a single intrinsically focused transducer is used, with the same inconvenients as above with regards to the stability of the cavitation zone. Some lighting means are provided in the form of a low intensity laser, for aiming the ultrasonic beam, and a light source, for illuminating an area to be viewed. These items are not mounted on a body of the device but connected to it via light guides, which is cumbersome. Moreover, the light is directed towards the skin, which is satisfactory for seeing a hair for epilation, but does not allow clearly seeing an object located below the skin, such as a vein. The light coming from the laser or the light source arrives in a central axial zone of the device, in the same zone as the boresight of a video camera. Thus, only direct illumination of the skin is possible.

Similar issues of potential hiding of a zone to be treated occur for the treatment of acne, wrinkles, cellulitis, tattoos, melanoma and lentigines.

SUMMARY OF THE INVENTION

This invention aims at solving the problems of the known techniques with a new device which is efficient to generate ultrasonic waves in a target region of a soft solid and allows a practitioner to precisely choose where ultrasonic waves focus, in particular for obtaining a cavitation phenomenon at one or several given points, below the skin surface of a patient.

To this end, the invention relates to a device for generating ultrasonic waves in a target region of a soft solid, this device including at least one ultrasound source for generating ultrasonic waves in the soft solid. According to the invention, the device includes at least two ultrasonic sources, preferably three ultrasonic sources, mounted on a body of the device and focused at a common focal point in the target zone, beyond an end surface of the device with respect to the ultrasonic sources. The device also includes lighting means, for enlightening a zone of the soft solid via subsurface scattering, and a video camera, for capturing images in the zone enlightened by the lighting means. The lighting means include several light sources distributed around a central axis of the device that includes a common focal point of all the ultrasonic sources. Moreover, the ultrasound sources, the light sources and the video camera are mounted on the body of the device and oriented towards the common focal point in the target zone. A boresight of the video camera is aligned on the central axis of the device.

Thanks to the invention, the light sources allow enlightening or illuminating a zone of the soft solid, in contact with the device, in particular the skin of a subject. These light sources also allow illuminating, by sub surface scattering (SSS), also known as subsurface light transport (SSLT), a portion of a muscle or tissue below the skin, which enables detection of spider veins and similar irregularities within a tissue such as acne, wrinkles, cellulitis, tattoos, melanoma and lentigines. In particular, in comparison to the teachings of EP-A-1 795 131 or WO-A-02/09813, operation of the device is not limited to seeing the skin of a patient. This derives from the fact that the different light sources distributed around the central axis have light beams that penetrate into the target region at several locations around the central axis, which induces a good illumination of the common focal point from different directions. Such an approach cannot be implemented if one uses a single light source, either centered on a central axis, as in WO-A-02/03813, or offset with respect to such an axis, as in EP-A-1 795 131. In addition, using at least two ultrasonic sources allows stabilizing the cavitation zone at their common focal point, which makes the device of the invention much easier to use than prior art systems. Thanks to the lighting means and embedded video camera of the invention, which are oriented towards the common focal point of the ultrasound sources, it is not necessary to use expansive pieces of equipment such as ultrasonic sensors or a Doppler camera, in order to efficiently position the device with respect to the soft solid. For instance, once the camera detects a vein or another irregularity in a tissue, the practitioner can use this detection to properly locate and/or move the device with respect to the tissue, in order to apply focused ultrasonic waves in the target region.

According to further aspects of the invention which are advantageous but not compulsory, the device might incorporate one or several of the following features, taken in any technically admissible configuration:

- A cavity, located in front of the or all ultrasonic source(s), is filled with a coupling medium and, in case this coupling medium is liquid, obturated by a membrane which belongs to an end surface of the device, is flexible, acoustically and optically transparent, has parallel main surfaces and a thickness below 100 µm, preferably below 50 µm, more preferably equal to about 35 µm.
- The coupling medium has an acoustic impedance between 1.45 and 1.65 $10^6 \cdot kg \cdot s^{-1} \cdot m^{-2}$, more preferably equal to about 1.54 $10^6 \cdot kg \cdot s^{-1} \cdot m^{-2}$, and is optically transparent.
- The light sources are distributed around the cavity.
- The light sources are mounted within a series or holes provided on said body or on a ring mounted around said body, said holes being distributed around the central axis in such a way that light beams emitted by the light sources do not cross the cavity.
- The boresight of the video camera crosses a transparent part, also mounted on the body and which separates the video camera from the cavity.
- The light source are made of LEDs.
- The wavelength of the light emitted by the LEDs is selected between 586 and 605 nm, in particular in the yellow and/or orange spectrum.
- The video camera has automatic gain control.
- The device includes detection means for detecting ultrasonic waves in the target region and means for providing a user with a signal representative of the level of scattered ultrasonic waves. The detection means advantageously include some ultrasonic transducers which also constitute the ultrasonic sources.
- The lighting means are mounted on a support member adapted to come into contact with and to bear against a surface of the soft solid.
- The body of the device is designed and configured to be held in one hand,
- The position and/or orientation of the video camera within the body of the device is adjustable.

The invention also relates to a system for generating ultrasonic waves in a target region of a soft solid, this system including a device as mentioned here-above and a screen for displaying images captured by the video camera.

Moreover, the invention concerns a method for locally treating a tissue of a subject, in particular by creating cavitation bubbles with ultrasonic waves, this method including at least the following steps:

a) placing a device in contact with a zone of the subject's skin;
b) actuating at least two ultrasound sources of the device oriented towards the subject's skin and focused at a common point in a target zone below the subjects' skin,
c) obtaining an image feedback of the tissue, in the target zone.

According to the invention,
this method includes a step d) of enlightening, via subsurface scattering, a zone of the tissue including a portion of the subject's skin in contact with the device and a layer of tissue below this portion,
step c) is implemented when step d) is implemented,
during step c), a video camera is used to capture images of the zone enlightened during step d),
this method also includes
a step e) of displaying to a user images captured by the video camera during step c) and
a further step f) where the user adjusts the placement of the device in contact with the subject's skin, on the basis of the displayed images.

BRIEF DESCRIPTION OF THE DRAWINGS

The invention will be better understood on the basis of the following description which is given in correspondence with the appended figures and as an illustrative example, without restricting the object of the invention. In the annexed figures.

DETAILED DESCRIPTION OF SOME EMBODIMENTS

Figure 1:
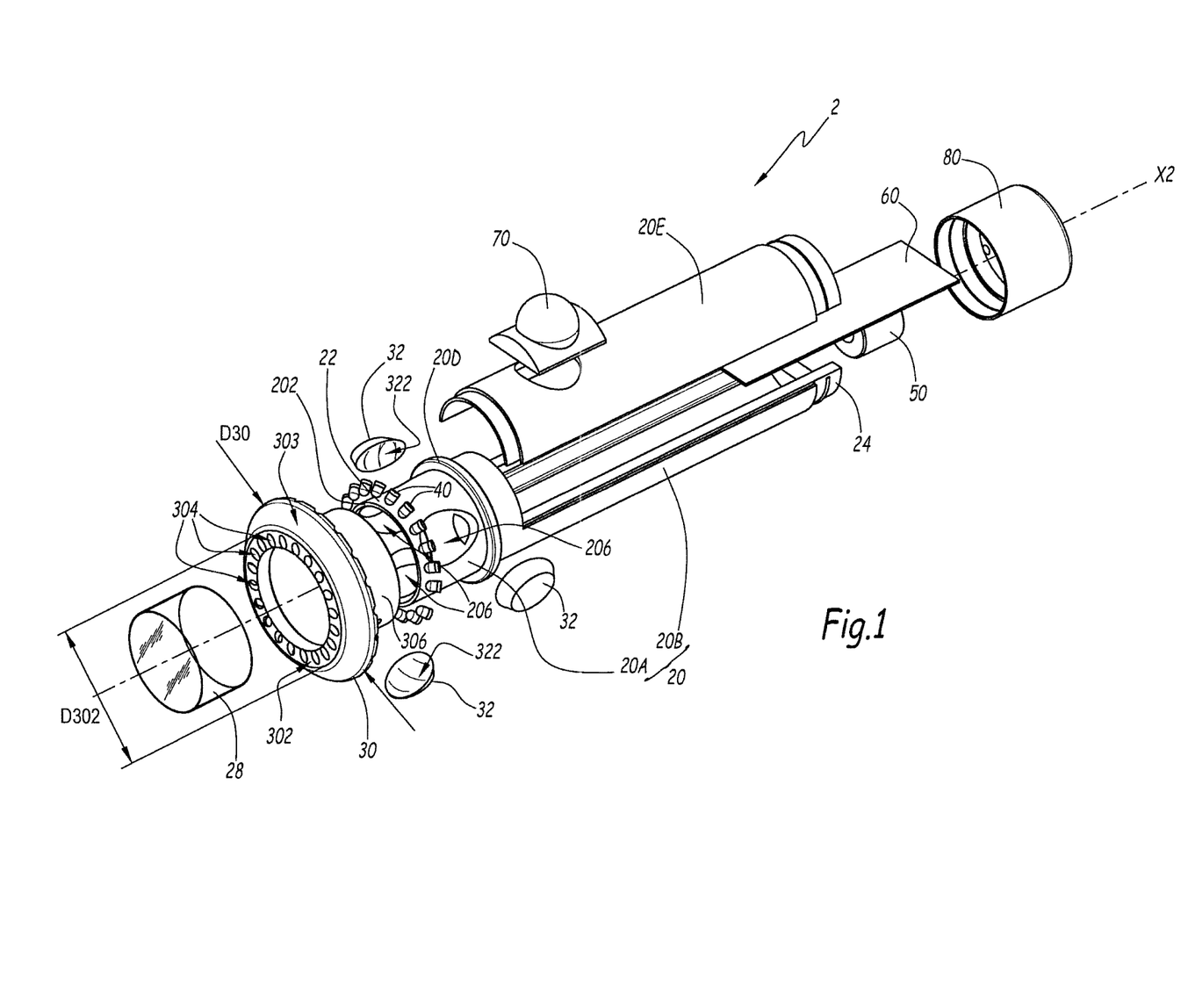
FIG. 1 is a perspective exploded view of a device according to a first embodiment of the invention.
Figures 2, 3:
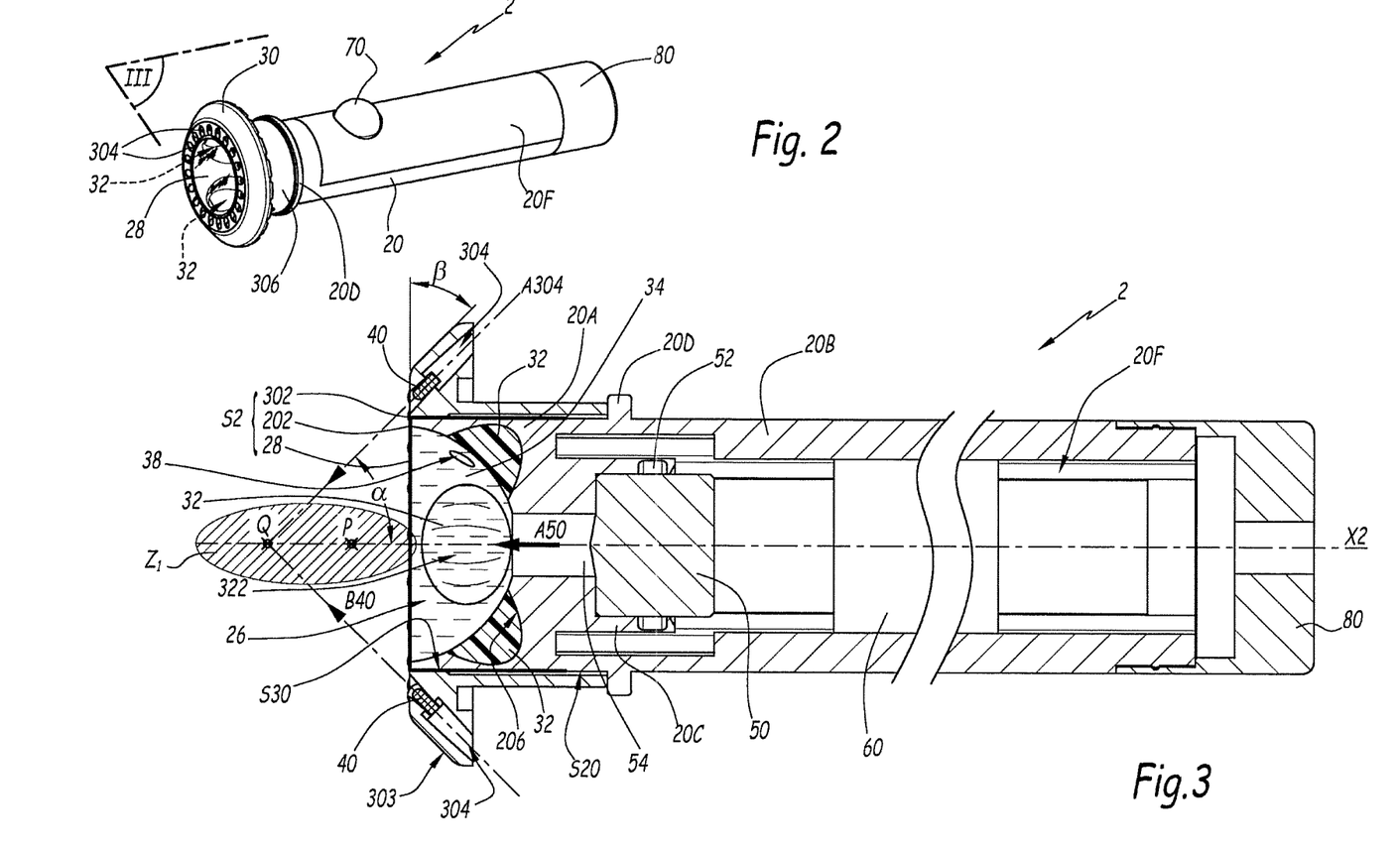
FIG. 2 is a perspective view of the device of FIG. 1 at a smaller scale.
FIG. 3 is a cut view along plane III on FIG. 2 at a larger scale.
Figure 4:
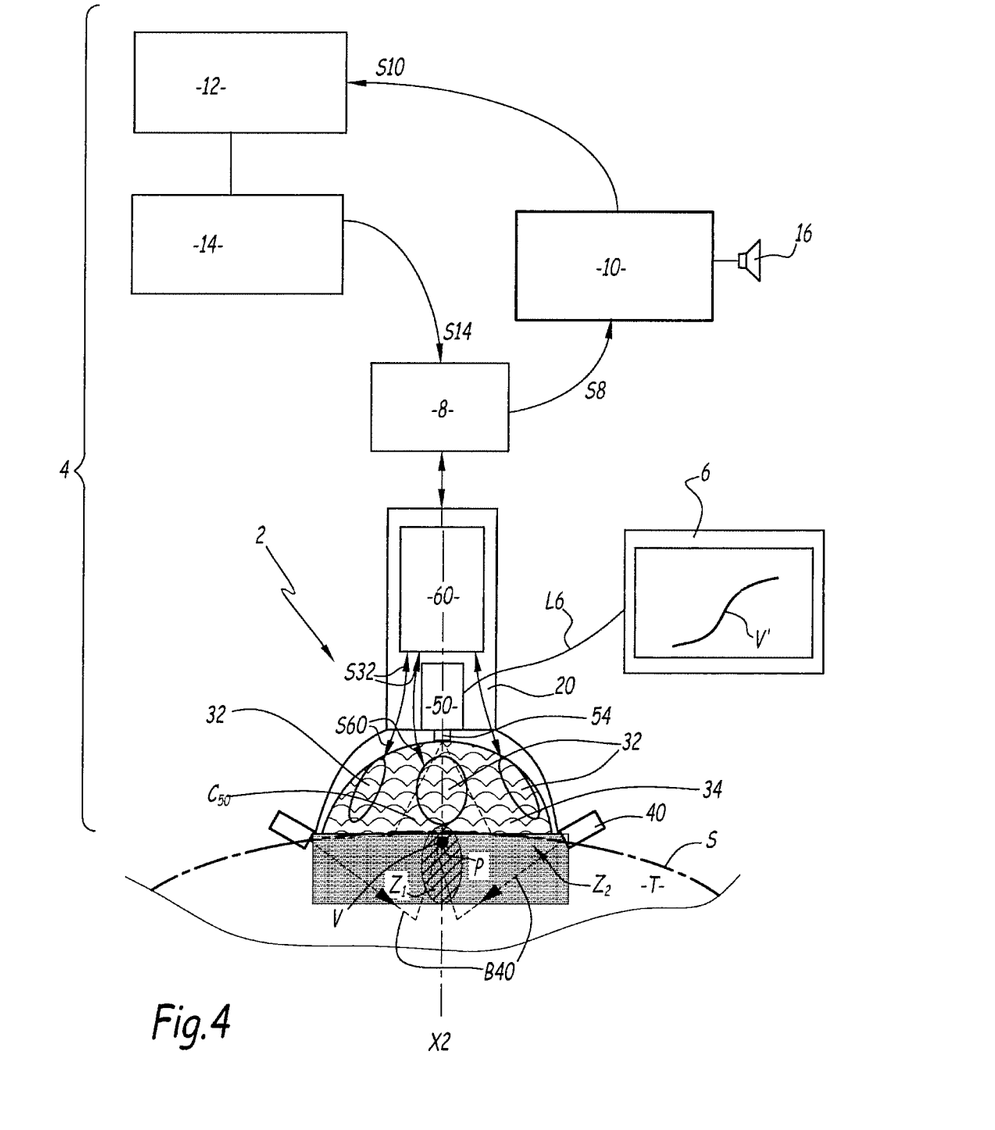
FIG. 4 is a schematic representation of the use of a system including the device of FIGS. 1 to 3.

The device 2 represented on FIGS. 1 to 3 constitutes a probe which belongs to a system schematically represented on FIG. 4.

FIGS. 1 to 3 show the structure of device 2, whereas FIG. 4 includes a functional representation of this device.

Device 2 includes a rigid body 20 made of a synthetic material such as plastic ABS or Nylon (registered trademark). This body 20 is centered on a longitudinal axis X2 and extends between a front end 22 and a rear end 24.

Next to front end 22, body 20 defines an opened cavity 26 which is obturated by a flexible membrane 28 made of an elastomer material such as silicone, polyester, poly(methyl) methacrylate or PMMA. Membrane 28 is optically transparent in the visible range.

Membrane 28 is held in position on front end 22 of body 20 by a retaining ring 30 which is mounted around a front portion 20A of body 20 and pinches membrane 28 around an outer radial surface S20 of this front portion.

Three piezoelectric ceramic transducers 32 are mounted within front portion 20A of body 20 with their active faces 322 oriented towards membrane 28 and towards axis X2. Transducers 32 are regularly distributed around axis X2. These three transducers 32 are designed and mounted onto body 20 in such a way that the ultrasonic waves respectively originating from these three ultrasound sources are focused and converge to a common focal point P which is located on axis X2, beyond membrane 28 with respect to transducers 32. Ultrasound sources formed by transducers 32 can also be said to be confocal at point P.

Transducers 32 work at a frequency between 0.1 and 10 MHz, preferably between 500 kHz and 3 MHZ and more preferably equal to about 1.6 MHz. Each time, a transducer 32 is actuated for a duration between 5 and 20 seconds.

Membrane 28 is also acoustically transparent in the frequency working range of transducers 32.

When it is mounted on body 20, ring 30 has an end face 302 which is flush with a terminal edge 202 of front portion 20A. Thus, edge 202 and end face 302 together define an end surface S2 of device 2 which is perpendicular to axis X2. Focal point P is beyond surface S2 with respect to the three ultrasound sources formed by transducers 32.

The active surface 322 of each transducer 32 is in the form of a portion of the sphere centered on this focal point. Actually, the wall of body 20 which defines cavity 26 may also be in the form of a portion of a sphere centered on this focal point P, which makes the assembly of device 2 easier. However, another shape is also possible for this cavity. Each transducer 32 is mounted within a housing formed by a hole 206 which extends through front portion 20A. When transducers 32 are mounted within their respective housings 206, their active surfaces 322 define, together with an inner surface of front portion 20A and membrane 28, cavity 26.

As visible on FIG. 3, ring 30 is provided, next to end face 302, with a reduced diameter inner radial surface S30 whose diameter is adjusted to the diameter of outer radial surface S20, so that membrane 28 is efficiently pinched between surfaces S30 and S20. Ring 30 also includes a skirt 306 which has an axial length, measured along axis X2, selected so that ring 30 bears against an annular outer collar 20D of body 20 when ring 30 is mounted around body 20. In this configuration, surface 302 is flush with edge 202, as mentioned here-above.

Actually, collar 20D separates front portion 20A and rear portion 20B of body 20.

Skirt 306 extends at a slight radial distance of surface S20, which avoids a risk of wedging ring 30 when it is mounted onto body 20.

On FIG. 1, membrane 28 is represented on the left of ring 30, that is in front of it. Actually, when it is mounted on body 20, membrane 28 is located at the level of surface 302 along axis X2 and radially between surfaces S20 and S30, where it is pinched. Thus, when it is mounted on body 20, membrane 28 belongs to end surface S2.

Cavity 26 is filled with a coupling medium, more particularly a coupling fluid, which allows ultrasonic waves originating from transducers 32 to propagate within cavity 26. The coupling fluid is selected in order not to attenuate, or to attenuate as little as possible, ultrasound waves coming from transducers 32. For instance, it can be made of water cleared of gases. Alternatively, the coupling medium can be made of a gel.

This coupling medium is selected in order to minimize reflection and refraction of ultrasounds on membrane 28 and in order to maximize ultrasound transmission through this membrane. This coupling medium is identified with reference 34 on FIGS. 3 and 4. It is optically transparent, at least in the visible range. Here-after, $Z_1$ denotes the acoustic impedance of a tissue to be treated with system 4 and $c_1$ denotes the ultrasound waves velocity within this tissue. Similarly, $Z_{34}$ and $c_{34}$ denote the acoustic impedance and ultrasound wave's velocity of medium 34. Considering the case where device 2 is used to treat varicose veins in a human body, and considering that transmission is optimal when $Z_{34}$ equals $Z_1$ and $c_{34}$ equals $c_1$, one chooses a coupling medium with an acoustic impedance between 1.35 and 1.65 $10^6 \cdot kg \cdot s^{-1} \cdot m^{-2}$, more preferably equal to about 1.54 $10^6 \cdot kg \cdot s^{-1} \cdot m^{-2}$. Thus, coupling medium 34 is acoustically transparent for the ultrasonic waves emitted by transducers 32, i.e. in the frequency working range of transducers 32.

Moreover, in order not to alter the acoustic waves coming out of transducers 32, membrane 28 is chosen with parallel main surfaces, at least in its portion perpendicular to axis X2. In other words, its main surfaces perpendicular to axis X2 are parallel to each other. Its thickness is below 100 micrometers (µm), preferably below 50 µm, more preferably equal to about 35 µm. The material of membrane 28 is preferably transparent to ultrasound waves.

A series of light sources formed by some LEDs 40 is mounted within ring 30. Actually, ring 30 is provided with twenty through-holes 304 and one LED 40 is installed within each through-hole. Through-holes 304 are regularly distributed around axis X2 when ring 30 is mounted on body 20. Through-holes are each aligned on an axis A304 and all axes A304 converge on a point Q which belongs to axis X2. As visible on FIG. 3, point Q is further away from membrane 28 and surface S2 than focal point P.

A target zone $Z_1$ is defined, which includes points P and Q and is centered on axis X2. Transducers 32 and LEDs 40 are oriented towards target zone $Z_1$. Target zone $Z_1$ is identified with hatches on FIGS. 3 and 4. Its actual shape depends on the structure and control of transducers 32 and LEDs 40.

LEDs 40 are oriented towards axis X2 and their respective light beams B40 converge to the front, towards this axis, with an angle of convergence α between 45 and 60°. In other words, these light beams B40 make an angle between 30 and 45° with the skin of a patient when device 2 is in use. This angle with the skin of a patient is also the angle between beams B40 and end face 302.

LEDs 40 are mounted on body 20 via ring 30.

LEDs 40 are used to enlighten or illuminate the skin of a subject or patient when device 2 is in use. Actually, LEDs 40 enlighten or illuminate not only the outer surface of the skin of the subject but also a portion of the tissue located below the skin, via sub surface scattering.

Device 2 also includes a video camera 50 which is mounted within body 20. In other words, video camera 50 is embedded in body 20. More precisely, body 20 has an inner cylindrical wall 20C which defines a recess, centered on axis X2 for accommodating video camera 50. An elastomeric gasket 52 is mounted within wall 20C and holds video camera 50 within the recess. Video camera works in the visible range. In practice, video camera 50 is a micro video camera, that is a camera with a length smaller than or equal to 20 mm, preferably 15 mm, and a diameter smaller than or equal to 25 mm, preferably 15 mm.

Video camera 50 is arranged within body 20 in such a way that its boresight is aligned with axis X2. The boresight of camera 50 is oriented towards membrane 28, in the direction of arrow A50 on FIG. 3. Thus, camera 50 is also oriented towards target zone $Z_1$. Camera 50 is separated from cavity 26 by a transparent part 54, more precisely a cylindrical part centered on axis X2 and made of poly(methyl) methacrylate or PMMA, also known as Plexiglas (registered trademark). This part 54 allows camera 50 capturing pictures through cavity 26 and membrane 28.

The low thickness of membrane 28 avoids perturbating waves going through this membrane, including ultrasonic waves coming from transducers 32 and images captured by video camera 50. In other words, no significant visual interference or sound attenuation is generated by membrane 28.

Device 2 also includes a printed circuit board or PCB 60 which is received within its rear portion 20B and which is used to control transducer 32 and camera 50 and to connect them to other parts of system 4.

Body 20 also includes a cover 20E which is adapted to be mounted on rear portion 20B once items 50 and 60 have been immobilized on body 20. A control switch 70 is mounted on cover 20E and is used by a practitioner in order to activate transducers 32 via PCB 60, when appropriate.

A rear cap 80 is mounted on rear end 24 and a rear portion of cover 20E. Rear cap 80 holds cover 20E in position with respect to the remaining portions of body 20. Apart from cover 20E, body 20 is integral. Rear cap 80 is provided with holes or connectors to allow electrical connection of device 2 to other parts of system 4 via electric lines which are not represented on FIGS. 1 to 3. One such hole is visible on FIG. 3. Actually, on FIGS. 1 to 3, no electric cable is represented, for the sake of clarity.

As shown on FIGS. 1 to 3, the general cylindrical shape of device 2 allows it to be held in one hand, with one finger pressing on switch 70 when necessary.

Body 20 is provided, in its surface defining cavity 26, with non represented recesses to accommodate bubbles potentially formed within medium 34 during use of device 2. Moreover, a channel is formed through body 20 in order to fill cavity 26 with coupling medium 34, the outlet of this channel is visible on FIG. 3, with reference 38.

In the use configuration shown on FIG. 4, PCB 60 is used to match the impedance in order to drive transducers 32 which generate acoustic waves focused on point P. On FIG. 4, arrows S60 represent the control of transducers 32 by PCB 60.

In the example of FIG. 4, a varicose vein V of a subject's tissue T is to be treated for destruction of its endothelium.

Camera 50 is used to efficiently locate or "place" device 2 with respect to tissue T, more particularly to its skin S, in order for this point P to coincide with varicose vein V or similar irregularities. When using system 4, the practitioner starts, in a first step a) represented on FIG. 8, by placing device 2 in contact with a primary zone of the patient's skin S where veins V to be treated are likely to be located. Identification of this primary zone can be performed with unaided eye.

Figure 8:
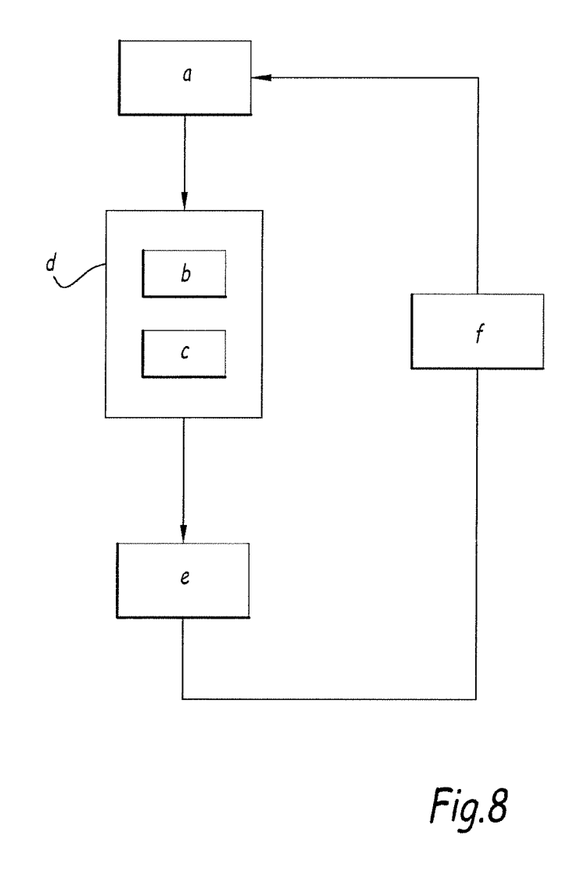
FIG. 8 is a bloc diagram of a method for using the device of FIGS. 1 to 3 or the device of FIGS. 5 to 7.

The method also includes a step b) where transducers 32 are actuated, in order to generate cavitation bubbles within the patient's body, as mentioned here-above.

A step c) is also implemented, where an image feedback of the tissue is obtained via camera 50.

In order for steps b) and c) to be realized efficiently, a step d) is implemented where LEDs 40 are actuated. During step b), the light beams B40 coming out of diodes 40 enlighten the portion of tissue T immediately adjacent to membrane 28 and to front end surface S2 of device 2, which allows camera 50 to capture images within a cone $C_{50}$ which represents its visibility zone. In other words, a zone $Z_2$ of tissue T, which is identified in grey on FIG. 4, is targeted or enlightened via diffusion of light by beams B40. This zone $Z_2$ includes a disc of skin S and a layer of tissue T below this disc. This allows video camera 50, which is a relatively simple and inexpensive device, to efficiently capture images allowing visualizing vein V.

Illumination of zone $Z_2$ by LEDs 40 occurs as long as camera 50 captures images. In other words, step c) occurs only when step d) is implemented.

Advantageously, step b) also occurs only when step d) is implemented.

System 4 also includes a screen 6 which is connected to video camera 50 via a connecting line L6 and where an image V' of vein V, captured by video camera 50, can be shown in a further step e) of the method. A user of system 4 who has device 2 in hand and watches screen 6 can thus adapt the position of device 2 with respect to tissue T, in a further step f), in order to efficiently treat vein V by focusing beams B40 on this part of tissue T. In other words, step f) is implemented by the practitioner using device 2 to adapt the placement of device 2 with respect to the patient's skin S and tissue T. During steps e) and f), steps b), c) and d) are still implemented. In particular, the user can move device 2 along vein V in order to make point P coincident with vein V on several locations, for treating this vein along its path within tissue T.

In order to take into account possible variations of the ambient lighting and possible variations of the response of the tissue T to the light emitted by LEDs 40, video camera 50 preferably has automatic gain control. This allows optimizing the contrast of the images to display the veins or irregularities on screen 6.

System 4 also includes a signal coupler 8, an electronic control unit 10 for acquiring and treating a signal S8 coming out of signal coupler 8, a signal generator 12 controlled by unit 10 via a control signal S10 and an amplifier 14 which delivers to coupler 8 an amplified signal S14.

According to an advantageous aspect of the invention, transducers 32 can also be used in order to control cavitation by monitoring ultrasonic waves within tissue T. In such a case, an output signal S32 of each transducer 32, which corresponds to the level of scattered ultrasonic waves, is delivered to PCB 60 which provides it to signal coupler 8 and electronic control unit 10. An output device, such as a loudspeaker 16, is used to inform the practitioner or user of system 4 of the efficiency of the cavitation level within tissue T. For instance, the level and/or frequency of the sound emitted by loudspeaker 16 can be based on the output signal S32 of transducers 32, thus be representative of the level of scattered ultrasonic waves.

Alternatively, instead of loudspeaker 16, other means can be used to inform the practitioner about the detected ultrasonic waves, such as a dedicated screen, a sub-screen of screen 6 or a LED or lamp visible by the practitioner which blinks when cavitation takes place, etc.

According to an alternative embodiment of the invention, sensors different from transducers 32 can be used in order to provide information to electronic control unit 10 with respect to the cavitation level within tissue T.

From a practical point of view, it appears that the wavelength of the light emitted by LEDs 40, which is in the visible range, can be selected between 586 and 605 nanometers (nm), in particular in the yellow and/orange spectrum, which allows an efficient illumination of zone $Z_2$, including by sub surface scattering or SSS.

As shown on FIG. 3, rear portion 20BA body 20 is provided with slides 20F for holding PCB 60 in position. These slides can also be used to house one or several tubes for feeding cavity 26 with coupling medium 34. In such a case, these tubes are connected to the channel whose outlet is visible with reference 38 on FIG. 3.

Ring 30 has a beveled surface 303 which converges towards end face 302. This allows surface 302, which defines the interface between device 2 and skin S during use of device 2, having a diameter D302 substantially smaller than the outer diameter D30 of ring 30 which cannot be reduced since LEDs 40 are accommodated within this ring. This enables reducing the friction surface on the skin S of the subject or patient to a disc of diameter D302. In practice, beveled surface 303 is dimensioned and oriented so that an angle β between surfaces 302 and 303 is between 30 and 45°.

Device 2 is easy to manipulate, with one hand, by a practitioner who can watch screen 6 as explained here-above. Device 2 is used as a big pen or probe, which is consistent with its ergonomics. Actually, depending on the habits of a practitioner, he/she might grip body 20 with different fingers so that the placement and displacement of device 2 with respect to tissue T might be different from one user to the other. In order to take this into account, and according to a non-represented aspect of the invention, the position and/or orientation of video camera 50 within body 20 is adjustable.

Since LEDs 40 are mounted within ring 30 which comes into contact with the skin S of a patient when the practitioner starts using device 2 and bears against skin S when lighting means are activated, the quantity of light transferred from LEDs 40 to enlightened zone $Z_2$ is maximal. This improves the quality of the images captured by video camera 50.

Figure 5:
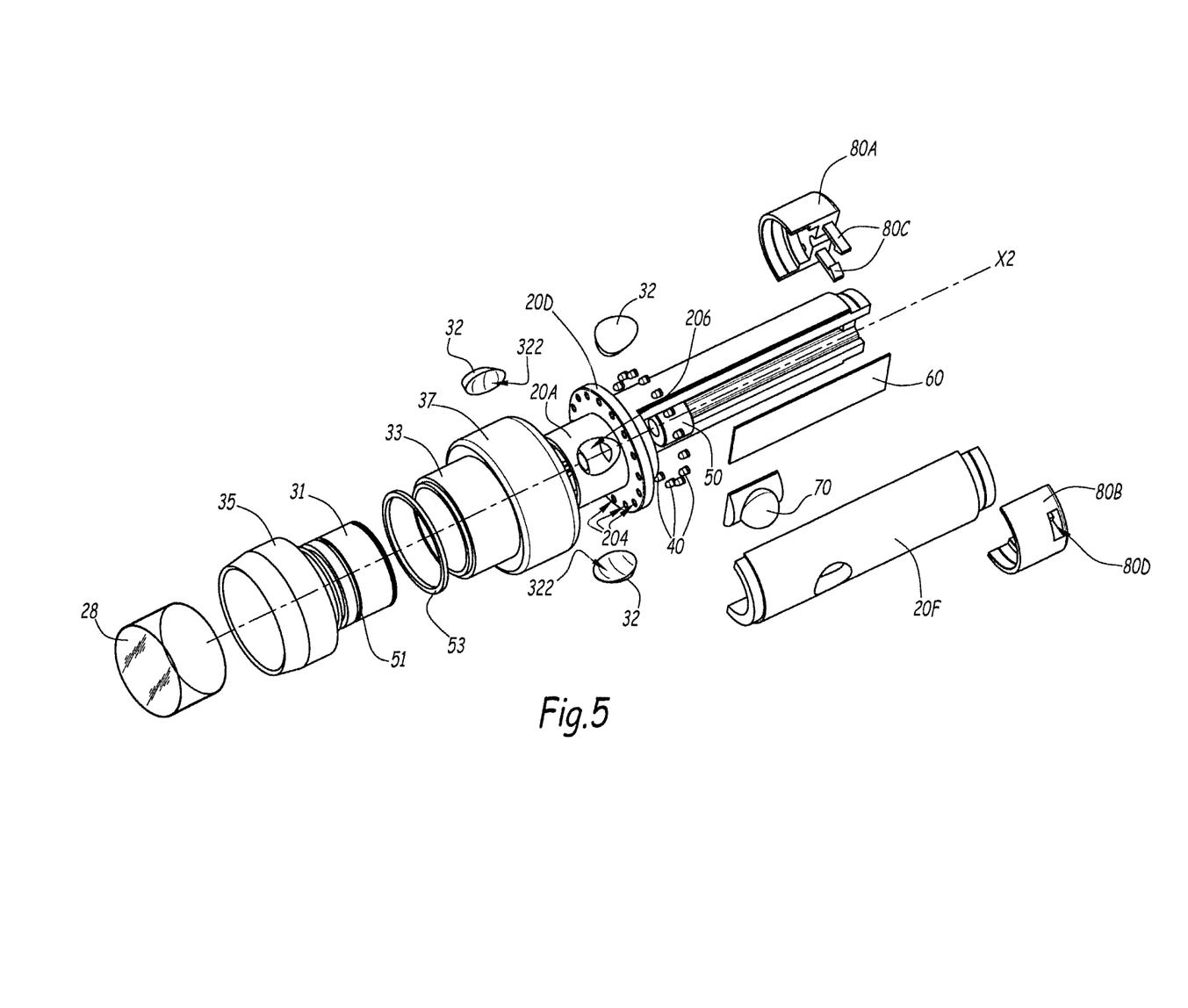
FIG. 5 is a perspective exploded view, similar to FIG. 1, for a device according to a second embodiment of the invention.
Figures 6, 7:
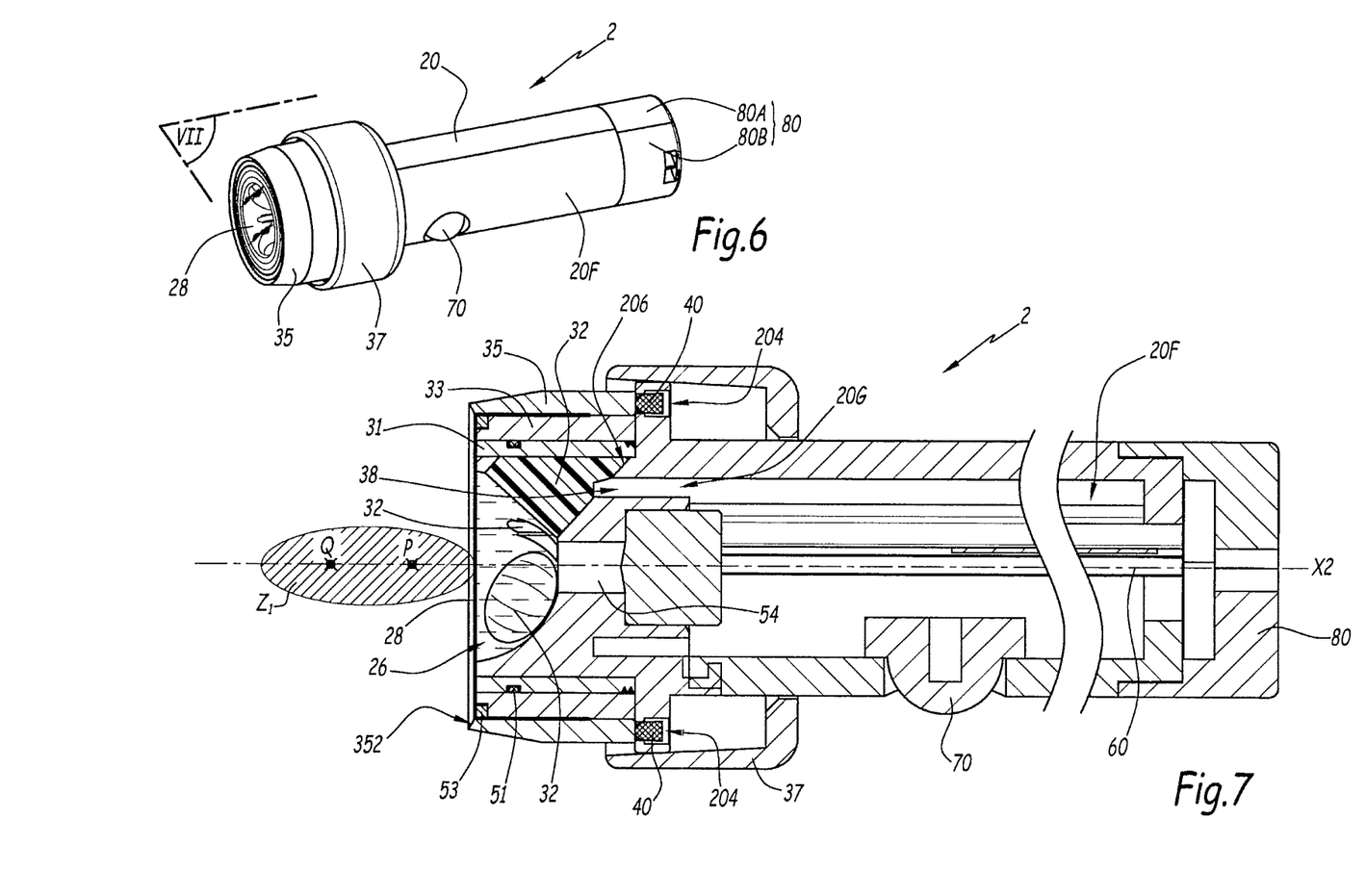
FIG. 6 is a perspective view of the device of FIG. 1 at a smaller scale.
FIG. 7 is a cut view along plane VII on FIG. 6 at a larger scale.

In the second embodiment of the invention represented on FIGS. 5 to 7, the portions of device 2 of the second embodiment which are similar to the ones of the first embodiment have the same references. This second device or probe 2 can also be used as a part of the system of FIG. 4 and works substantially as device 2 of the first embodiment. Here-after, only the differences with the first embodiment are explained.

The rear cap 80 is formed of two halves 80A and 80B which are clipped together by elastic tongues 80C and corresponding recesses 80D. In this embodiment, the LEDs 40 are received within through holes 204 evenly distributed around axis X2 and provided within collar 20D.

FIG. 7 shows one slide 20F of body 20 aligned with a channel 20G which has an outlet 38 connected to cavity 26. A non represented tube can be installed within slide 20F in order to feed channel 20G and cavity 26. This cavity is made within a front portion 20A of body 20 surrounded by three rings, namely an inner ring 31, an intermediate ring 33 and an outer ring 35. A holding member 53 is provided at the interface between rings 33 and 35. Ring 35 is aligned, along a direction parallel to axis X2, with light sources constituted by LEDs 40 and forms a wave guide for the light emitted by these LEDs, towards an end surface S2 of device 2.

This second embodiment has been designed to be compatible with an adjustment of the axial distance defined between focal point P and membrane 28, allowing the practitioner to adjust depth of penetration of the cavitation into tissue T. This is to treat more or less deep veins. For that purpose ring 31 is designed with an external thread which fits with an internal thread provided on ring 33. This ring 33 is also equipped with a circumferential groove 51 in which a non-represented O-ring is inserted. Ring 31 is hermetically bonded on front portion 20A of body 20. Ring 33 is screwed on ring 31 and membrane 28 is pinched by holding member 53 on ring 33 or bonded directly on the holding member 53. This assembly can be filled with coupling liquid and remains hermetic whatever the position of the ring 33 along axis X2 is, thanks to O-ring located in groove 51. Ring 35 is made of a transparent material, like PMMA or another transparent plastics. It is inserted on ring 33 and insures conduction of the light emitted by the LEDs 40.

The front edge 352 of outer ring 35 is beveled rearwardly towards axis X2 and membrane 28 is pinched between rings 35 and 33.

A ring 37 is mounted around rear portion 20B and collar 20D of body 20 and protects LEDs 40 and their wiring against contact with the user. As in the first embodiment, transducers 32 which form ultrasound wave sources, LEDs 40 and video camera 50 are mounted on body 20. In this case, LEDs 40 are directly mounted within holes 204 formed in body 20, whereas in the first embodiment, LEDs 40 are mounted on body 20 via ring 30 which is immobilized onto this body.

In this second embodiment, transducers 32, LEDs 40 and camera 50 are also oriented towards a target zone $Z_1$ visible on FIG. 6, which includes focal point P of transducers 32 and convergence point Q of LEDs 40.

Device 2 of this second embodiment can be used to implement the method of FIG. 8.

In both embodiments, the use of LEDs as lighting means is advantageous in terms of life time and because of the relatively low temperature of a diode, as compared to an incandescent bulb, which avoids burning the skin of a patient. Moreover, the lighting power of LEDs can be easily adjusted.

In both embodiments, the fact that the boresight of video camera 50 is aligned on central axis X2 induces that this boresight is globally perpendicular to the skin 5 of the patient when device 2 is in use. This makes it more intuitive to use.

In both embodiments, since LEDs 40 are located around transducers 32, light beams B40 do not have to cross cavity 26. This avoids reflection issues with respect to light beams B40 crossing coupling medium 34, whereas such a reflection could alter the quality of the images captured by video camera 50.

The invention is explained here above in case device 2 includes three ultrasound sources formed by transducers 32. However, it can also work with a single ultrasound source, with two such sources or with four such sources or more. With a single transducer used as an ultrasound source, the bubbles can be pushed away by a radiation force. This is why, in such a case, one should prefer a highly focalized ultrasound source. The interest of using several ultrasound sources is to create a network of interferences in a focal zone, where the cavitation bubbles can be trapped. Another interest of this approach is to reduce the size of the focal volume for improving treatment spatial resolution.

The invention is explained here-above in case video camera works in the visible range. Alternatively, an infra-red (IR) video camera can be used. In such a case, membrane 28 and coupling medium 34 are optically transparent in the IR range and the light used to enlighten zone $Z_2$ is adapted.

According to another approach, a lighting light with a different wavelength, e.g. ultraviolet, might be used to highlight a specific target. This could be coupled to the injection of a fluorescent agent.

The invention is explained here above in case it is used for treating a varicose vein. It can also be used for the treatment of acne, wrinkles, cellulites, tattoos, melanoma and/or lentigines. It can also be used for generating ultrasonic waves in a human or animal body.

According to a non represented alternative embodiment of the invention, the coupling medium which fills cavity 26 can be solid. In such a case, membrane 28 can be omitted.

The embodiments and alternative embodiments considered here-above can be combined to generate new embodiments of the invention.

The invention claimed is:

1. A device for generating ultrasonic waves in a soft solid, the device comprising:
   a body, extending between a front end and a rear end, comprising a front portion having an outer surface extending to the front end and aligned to a central axis, and an inner cavity surface extending inward from a cavity opening at the front end;
   a ring aligned to the central axis, surrounding the front portion's outer surface;
   a membrane, which is transparent, mounted to the body such that a region of the membrane obturates the cavity opening and defines, in combination with the inner cavity surface, a cavity;
   a plurality of ultrasonic transducers, mounted in the inner cavity surface in an arrangement that generates ultrasonic waves that transmit from the cavity opening, through the region of the membrane, in respective directions that focus the ultrasonic waves at a common focal point, beyond the front end;
   a plurality of light sources, mounted to the ring in a distribution around the central axis and outside the cavity opening, and with respective orientations, the distribution and orientations configured to converge light beams from the plurality of light sources on a convergence point in the soft solid, the convergence point being spaced further from the membrane and from the front end of the body than the common focal point is spaced from the membrane and from the front end of the body, wherein the light sources and their respective distribution and orientations are configured such that the light beams enlighten a zone of the soft solid containing the convergence point and the common focal point; and
   a video camera, arranged in the body separated from the cavity in a direction toward the rear end of the body by an optically transparent member, the video camera having a boresight that is aligned with the central axis and crosses the optically transparent member,
   wherein:
   the video camera is configured to capture, through the membrane and the optically transparent member, images from the zone in the soft solid when the zone is enlightened by the plurality of light beams from the light sources,
   the cavity is filled with a fluid coupling medium, and
   the distribution and orientations of the light sources are further configured such that the light beams do not cross into the cavity.

2. A device according to claim 1, wherein the fluid coupling medium has an acoustic impedance between 1.45 and 1.65 $10^6 \cdot kg \cdot s^{-1} \cdot m^{-2}$.

3. A device according to claim 1, wherein:
   the membrane has an outer region that extends beyond the cavity opening and over the outer surface at the front end of the body; and
   the ring is arranged over the outer surface at the front end of the body, in a configuration pinching, between an inner surface of the ring and the outer surface at the front end of the body, region of the membrane, maintaining the membrane against and obturating the cavity opening.

4. A device according to claim 1, wherein the light sources comprise light emitting diodes (LEDs), and wherein the wavelength of light emitted by the LEDs is between 586 and 605 nm.

5. A device according to claim 1, wherein the video camera has automatic gain control.

6. A device according to claim 1, wherein the ultrasonic transducers are configured to detect scattered ultrasonic waves in the soft solid, arising from the ultrasonic waves transmitted by the device, and wherein the device further comprises a loudspeaker, a screen, a sub-screen, a light emitting diode (LED) or a lamp configured to provide a user with a signal representative of a level of the scattered ultrasonic waves.

7. A device according to claim 1, wherein the ring includes a front edge, at the front end of the body, which is adapted for contacting and bearing against a surface of the soft solid.

8. A device according to claim 1, wherein the body is configured as holdable in one hand.

9. A device according to claim 1, wherein the video camera is mounted to the body by a mount providing an adjustable position and/or orientation of the video camera within the body.

10. A system for generating ultrasonic waves in a soft solid, the system including:
    a device according to claim 1, and
    a screen for displaying images captured by the video camera of the device.

11. A method for locally treating a tissue of a subject, in particular by creating cavitation bubbles with ultrasonic waves, comprising:
    placing a device according to claim 1 in contact with a portion of the subject's skin above the tissue, wherein the soft solid is the tissue, in an orientation that positions the common focal point within the tissue, and aligns the convergence point below the common focal point;
    enlightening the zone by steps comprising actuating the plurality of light sources to output the light beams that, via convergence at the convergence point and subsurface scattering, enlighten the zone;
    generating cavitation bubbles, by steps comprising actuating the at least two ultrasonic transducers of the device to output respective ultrasonic wave focused at the common focal point, while the device is in said orientation concurrent with enlightening the zone;
    capturing by the video camera, as feedback images, images of tissue in the zone, concurrent with generating the cavitation bubbles;
    displaying, to a user, the feedback images captured by the video camera during capturing; and
    adjusting a placement of the contact of the device on the subject's skin, or the orientation of the device when in contact with the subject's skin, or both, in accordance with the displayed feedback images.

12. A device according to claim 1, wherein the plurality of ultrasonic transducers comprises three ultrasonic transducers.

13. A device according to claim 1, wherein the region of the membrane that obturates the cavity opening has parallel main surfaces that are spaced apart by a thickness of 35 μm.

14. A device according to claim 1, wherein the arrangement of the ultrasonic transducers and the distribution and orientations of the plurality of light sources are in a mutual configuration that, when the ultrasonic transducers are generating the ultrasonic waves while the front end of the device is against a surface of the soft solid with the device positioned and oriented to place the common focal point within the zone, places the convergence point of the light beams below the common focal point.

15. A device according to claim 1, wherein the distribution and the orientations of the light sources are further configured such that, when the device is against a skin surface of a patient, positioned and oriented to place the convergence point under the common focal point, the light beams from the light sources converge with an angle of convergence between 45° and 60°.

16. A device according to claim 1, wherein the distribution and the orientations of the light sources are further configured such that, when the device is against a skin surface of a patient, positioned and oriented to place the convergence point under the common focal point, the light beams make an angle between 30° and 45° with the skin surface of the patient.

17. The device of claim 1, wherein the ring is an outer ring positioned at the front end of the body, wherein the device further comprises:
an inner ring that is bonded to the front end of the body and has an inner ring outer cylindrical surface;
an intermediate ring, having an intermediate ring inner cylindrical surface and an intermediate ring outer cylindrical surface, which is arranged over the inner ring in a configuration wherein the intermediate ring inner cylindrical surface surrounds the inner ring outer cylindrical surface,
wherein
the outer ring surrounds the intermediate ring outer cylindrical surface,
a region of the inner ring outer cylindrical surface carries external threads,
a region of the intermediate ring inner cylindrical surface carries internal threads, that are in a threaded engagement with the external threads of the inner ring,
the outer ring and the inner ring are in a mutual arrangement wherein rotating of the outer ring effects a rotating the intermediate ring, effecting a rotating of the threaded engagement between the inner threads of the intermediate ring and the outer threads of the inner ring,
wherein the internal threads of the intermediate ring and the external threads of the inner ring are mutually configured to translate the rotating of the threaded engagement to an axial movement of the outer ring and the intermediate ring relative to the ultrasonic transducers mounted in the cavity surface acoustic, that correspondingly changes both an axial distance from the ultrasonic transducers to the membrane at the front end of the device and an axial distance from the membrane to the common focal point.

18. A device according to claim 2, wherein the coupling medium has an acoustic impedance equal to 1.54 $10^6 \cdot kg \cdot s^{-1} \cdot m^{-2}$.

19. The device of claim 4, wherein the light sources comprise light emitting diodes (LEDs), and the wavelength of light emitted by the LEDs is in the yellow and/or orange spectrum.

20. The device of claim 17, wherein:
the membrane has an outer region that extends beyond the cavity opening and over an outer surface at the front end of the body,
the outer ring has an outer ring inner cylindrical surface that surrounds the intermediate ring outer cylindrical surface,
the membrane, the intermediate ring outer cylindrical surface, and the outer ring inner cylindrical surface have a mutual configuration that maintains the membrane against and obturating the cavity opening, by a pinching of the outer region of the membrane between the inner cylindrical surface of the outer ring and the outer cylindrical surface of the intermediate ring.

21. A method for locally treating a tissue of a subject, in particular by creating cavitation bubbles with ultrasonic waves, comprising:
placing a device according to claim 17 in contact with a portion of the subject's skin above the tissue, wherein the soft solid is the tissue, in an orientation that positions the common focal point within the tissue, and aligns the convergence point below the common focal point;
enlightening the zone, by steps comprising actuating the plurality of light sources to output the light beams that, via convergence at the convergence point and subsurface scattering, enlighten the zone;
generating cavitation bubbles, by steps comprising actuating the at least two ultrasonic transducers of the device to output respective ultrasonic wave focused at the common focal point, while the device is in said orientation concurrent with enlightening the zone;
capturing by the video camera, as feedback images, images of tissue in the zone, concurrent with generating the cavitation bubbles;
displaying, to a user, the feedback images captured by the video camera during capturing;
adjusting a placement of the contact of the device on the subject's skin, or the orientation of the device when in contact with the subject's skin, or both, in accordance with the displayed feedback images; and
adjusting a depth of the penetration of the cavitation bubbles by operations comprising rotating, via rotating the outer ring, the threaded engagement between the inner threads of the intermediate ring and the outer threads of the inner ring.

22. A device for generating ultrasonic waves in a region of a soft solid, the device comprising:
a body that extends along a central axis from a front end to a rear end, having a front portion that extends to the front end and has an outer surface, and the front end portion including an inner cavity surface, aligned with the central axis and extending toward the rear end from a cavity opening at the front end;
a membrane that is mounted to the front portion of the body in an arrangement wherein a region of the membrane obturates the cavity opening and, in combination with the inner cavity surface, defines a cavity, the membrane being optically and acoustically transparent;
a plurality of ultrasonic transducers, configured to generate respective ultrasonic waves, and mounted in the inner cavity surface in an arrangement wherein the ultrasonic waves transmit from the cavity opening and focus at a common focal point beyond the front end of the device;
a ring, aligned with the central axis, the ring including a transparent waveguide ring structure and surrounding the cavity opening and the outer surface of the front portion;
a plurality of light sources mounted to the transparent waveguide ring structure and configured to generate respective light beams; and a video camera, arranged in the body separated from the cavity in a direction toward the rear end of the body by an optically transparent member, the video camera having a boresight that is aligned with the central axis and crosses the optically transparent member, wherein the transparent waveguide ring structure is configured to receive the light beams from the light sources, and guide and output the received light beams from surface locations on the transparent waveguide ring structure around the cavity opening, as transmitted light beams that:

converge on a convergence point aligned with the central axis and spaced further from the membrane and from the front end of the body than the common focal point is spaced from the membrane and from the front end of the body, and have respective distribution and orientations that are configured such that the light beams enlighten a zone of the soft solid containing the convergence point and the common focal point, and the video camera is configured to capture, through the membrane and the optically transparent member, images from the zone when the zone is enlightened by the plurality of light beams from the light sources.

23. A device according to claim 22, wherein the ultrasonic transducers are further configured to detect scattered ultrasonic waves in the soft solid, arising from the ultrasonic waves transmitted by the device, and wherein the device further comprises a loudspeaker, a screen, a sub-screen, a light emitting diode (LED) or a lamp configured to provide a user with a signal representative of a level of the scattered ultrasonic waves.

24. A device according to claim 22, wherein the device further comprises:

wherein the fluid coupling medium has an acoustic impedance between 1.45 and 1.65 $10^6 \cdot kg \cdot s^{-1} \cdot m^{-2}$.

25. A device according to claim 22, wherein the video camera has automatic gain control.

26. A device according to claim 22, wherein the video camera is mounted to the body by a mount providing an adjustable position and/or orientation of the video camera within the body.

27. A method for locally treating a tissue of a subject, in particular by creating cavitation bubbles with ultrasonic waves, comprising:

placing a device according to claim 22 in contact with a portion of the subject's skin above the tissue, wherein the soft solid is the tissue, in an orientation that positions the common focal point within the tissue, and aligns the convergence point below the common focal point;

enlightening the zone, by steps comprising actuating the plurality of light sources to output the light beams that, via convergence at the convergence point and subsurface scattering, enlighten the zone;

generating cavitation bubbles, by steps comprising actuating the at least two ultrasonic transducers of the device to output respective ultrasonic wave focused at the common focal point, while the device is in said orientation concurrent with enlightening the zone;

capturing by the video camera, as feedback images, images of tissue in the zone, concurrent with generating the cavitation bubbles;

displaying, to a user, the feedback images captured by the video camera during capturing; and adjusting a placement of the contact of the device on the subject's skin, or the orientation of the device when in contact with the subject's skin, or both, in accordance with the displayed feedback images.

28. A device according to claim 22, wherein the ring is an outer ring positioned at the front end of the body, wherein the device further comprises:

an inner ring that is bonded to the front end of the body and has an inner ring outer cylindrical surface;

an intermediate ring, having an intermediate ring inner cylindrical surface and an intermediate ring outer cylindrical surface, arranged over the inner ring in a configuration wherein the intermediate ring inner cylindrical surface surrounds the inner ring outer cylindrical surface, wherein the outer ring surrounds the intermediate ring outer cylindrical surface, a region of the inner ring outer cylindrical surface carries external threads, a region of the intermediate ring inner cylindrical surface carries internal threads, which are in a threaded engagement with the external threads of the inner ring, the outer ring and the inner ring are in a mutual arrangement wherein rotating of the outer ring effects a rotating the intermediate ring, effecting a rotating of the threaded engagement between the inner threads of the intermediate ring and the outer threads of the inner ring, wherein the internal threads of the intermediate ring and the external threads of the inner ring are mutually configured to translate the rotating of the threaded engagement to an axial movement of the outer ring and the intermediate ring relative to the ultrasonic transducers mounted in the cavity surface acoustic, that correspondingly changes both an axial distance from the ultrasonic transducers to the membrane at the front end of the device and an axial distance from the membrane to the common focal point.

29. A device according to claim 24, wherein the fluid coupling medium has an acoustic impedance equal to 1.54 $10^6 \cdot kg \cdot s^{-1} \cdot m^{-2}$.

30. A system for generating ultrasonic waves in a region of a soft solid, the system including:

a device according to claim 22, and a screen for displaying images captured by the video camera of the device.

31. A device according to claim 28, wherein:

the membrane has an outer region that extends beyond the cavity opening and over an outer surface at the front end of the body, the outer ring has an outer ring inner cylindrical surface that surrounds the intermediate ring outer cylindrical surface, the membrane, the intermediate ring outer cylindrical surface, and the outer ring inner cylindrical surface have a mutual configuration that maintains the membrane against and obturating the cavity opening, by a pinching of the outer region of the membrane between the inner cylindrical surface of the outer ring and the outer cylindrical surface of the intermediate ring.

32. A method for locally treating a tissue of a subject, in particular by creating cavitation bubbles with ultrasonic waves, comprising:

placing a device according to claim 28 in contact with a portion of the subject's skin above the tissue, wherein the soft solid is the tissue, in an orientation that positions the common focal point within the tissue, and aligns the convergence point below the common focal point;

enlightening the zone, by steps comprising actuating the plurality of light sources to output the light beams that, via convergence at the convergence point and subsurface scattering, enlighten the zone;

generating cavitation bubbles, by steps comprising actuating the at least two ultrasonic transducers of the device to output respective ultrasonic wave focused at the common focal point, while the device is in said orientation concurrent with enlightening the zone;

capturing by the video camera, as feedback images, an image of tissue in the zone, concurrent with generating the cavitation bubbles;

displaying, to a user, the feedback images captured by the video camera during capturing;

adjusting a placement of the contact of the device on the subject's skin, or the orientation of the device when in contact with the subject's skin, or both, in accordance with the displayed feedback images; and adjusting a depth of the penetration of the cavitation bubbles by operations comprising rotating, via rotating the outer ring, the threaded engagement between the inner threads of the intermediate ring and the outer threads of the inner ring.

\* \* \* \* \*